(12) United States Patent
Yugawa et al.

(10) Patent No.: US 7,241,578 B2
(45) Date of Patent: Jul. 10, 2007

(54) IMMUNOASSAY METHOD/EQUIPMENT, BIOLOGICAL COMPONENT MEASURABLE TOILET, ANTI-ALBUMIN MONOCLONAL ANTIBODY, CELL STRAIN PRODUCING THE SAME, AND ALBUMIN DETECTION KIT

(75) Inventors: Keiko Yugawa, Nara (JP); Nobuyuki Shigetoh, Kyoto (JP); Akihito Kamei, Kyoto (JP); Tatsurou Kawamura, Kyoto (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 533 days.

(21) Appl. No.: 10/441,192

(22) Filed: May 20, 2003

(65) Prior Publication Data

US 2003/0219910 A1   Nov. 27, 2003

(30) Foreign Application Priority Data

May 22, 2002  (JP) ............................ 2002-148297
May 9, 2003   (JP) ............................ 2003-131790

(51) Int. Cl.
| G01K 33/53 | (2006.01) |
| G01K 33/536 | (2006.01) |
| G01K 33/557 | (2006.01) |
| G01K 33/577 | (2006.01) |
| C07K 16/18 | (2006.01) |
| C12N 5/20 | (2006.01) |
| C12P 21/08 | (2006.01) |

(52) U.S. Cl. ..................... 435/7.1; 435/7.8; 435/70.21; 435/452; 435/337; 436/517; 436/518; 436/536; 436/537; 436/539; 436/548; 436/164; 530/388.25

(58) Field of Classification Search ................. 435/7.1, 435/7.8, 70.21, 452, 337; 436/517, 518, 436/536, 537, 539, 548, 164; 530/388.25
See application file for complete search history.

(56) References Cited

U.S. PATENT DOCUMENTS

| 4,618,589 A | * | 10/1986 | Jefferis et al. ............... 436/540 |
| 4,860,767 A | | 8/1989 | Maekawa |
| 5,420,042 A | * | 5/1995 | Schafer et al. ............... 436/517 |
| 6,136,545 A | | 10/2000 | Hosel et al. |
| 2001/0031913 A1 | | 10/2001 | Ito et al. |

FOREIGN PATENT DOCUMENTS

| EP | 0 161 638 | * 11/1985 |
| JP | 2515533 | 4/1996 |
| JP | 2607363 | 2/1997 |

OTHER PUBLICATIONS

Marre et al., 1987. Laser immunonephelometry for routine quantification of urinary albumin excretion. Clin. Chem. 33 (2): 209-213.*
Nakamura et al., 1998. Liquid-phase binding assay of alpha-fetoprotein using a sulfated antibody for bound/free separation. Anal. Chem. 70: 954-957.*
Harmoinen et al., 1987. Turbidimetric measurement of microalbuminuria. Clinica Chimica Acta 166: 85-89.*
Kazuyoshi Hatsuda, et al., "Development of Turbidimetricassay for Urine Albumin Using Polyclonal and Monoclonal Antibody," transaction of The Institute of Japan Clinical Chemistry, 28th Annual Conference, p. 125, 1988.
Hud E et al., "Evaluation and Performance Characteristics of a Novel Elisa Using Monoclonal Antibody to Glycated Albumin" Clinica Chimica Acta, Amsterdam, NL, vol. 185, No. 2, Nov. 1, 1989, pp. 157-164.
Angelisova P et al., "The Characteristics of Monoclonal Antibodies Against Human Albumin." Folla Biologica (Prague), vol. 32, No. 5, 1988, pp. 289-294.
"Use of Monoclonal antibody in ELISA for the detection of microalbumin in urine," Nov. 1, 1996, pp. 17-18.

* cited by examiner

*Primary Examiner*—Long V. Le
*Assistant Examiner*—James L. Grun
(74) *Attorney, Agent, or Firm*—McDermott Will & Emery LLP (57) ABSTRACT

The immunoassay method of this invention measures the content of a subject substance in a sample. The method includes the steps of: (a) preparing a mixed solution by mixing the sample and an antibody solution including a first monoclonal antibody and a second monoclonal antibody capable of specifically binding to the subject substance; and (b) measuring an optical property of the mixed solution. The first monoclonal antibody is capable of binding to a first epitope of the subject substance, and the second monoclonal antibody is capable of binding to a second epitope of the subject substance different from the first epitope. Each of the first and second epitopes exists singly in the subject substance.

13 Claims, 9 Drawing Sheets

IMMUNOASSAY METHOD/EQUIPMENT, BIOLOGICAL COMPONENT MEASURABLE TOILET, ANTI-ALBUMIN MONOCLONAL ANTIBODY, CELL STRAIN PRODUCING THE SAME, AND ALBUMIN DETECTION KIT

BACKGROUND OF THE INVENTION

The present invention relates to an immunoassay method for measuring a specific component in a sample.

Conventionally, various immunoassay methods using antibodies have been proposed as methods for measuring a specific component (subject substance) in a sample easily without involving dilution or agitation of a sample liquid.

Immunoturbidimetry is known as one of the immunoassay methods. An assay kit used for immunoturbidimetry (Microalbumin-HA TestWako of Wako Pure Chemicals Industries, Ltd) is commercially available. This assay kit is essentially composed of a buffer (50 mM Good's buffer, pH 7.4) and an antibody solution. The antibody solution includes a rabbit-derived anti-human albumin polyclonal antibody (1.5 mg Ab/ml) and a mouse-derived anti-human albumin monoclonal antibody (4.0 mg Ab/ml). In measurement, a sample is allowed to act with the antibody solution in the buffer. If albumin is included in the sample, the albumin specifically reacts with the anti-human albumin antibodies as an antigen-antibody reaction, turning the solution turbid. The degree of being turbid (turbidity) is proportional to the concentration of albumin in the sample. By measuring the turbidity, therefore, the albumin amount in the sample can be determined.

The reason why the assay kit described above uses both the polyclonal antibody and the monoclonal antibody is considered to combine the feature of the former of "enhancing the turbidity" and the feature of the latter of "causing less easily a prozone phenomenon". That is, the combination of the polyclonal antibody and the monoclonal antibody for simultaneous use can broaden the measurable range while preventing occurrence of the prozone phenomenon in an antigen excess region, which is a shortcoming of the immunoturbidimetry (see K. Hatsuta et al., The 28th Japan Society of Clinical Chemistry Meeting Proceedings, 63, 1988, p. 125).

The immunoturbidimetry described above theoretically permits measurement of various substances, by selecting an antibody binding to a subject substance to be measured for each subject substance. For example, if an anti-human albumin antibody is selected as the antibody, a sensor for measuring the concentration of albumin in a sample liquid can be produced.

Albumin is a protein occupying about 50% of the protein in plasma that is the remainder of blood obtained after removing solid components such as blood cells. Albumin is known to have functions such as maintenance of the osmotic pressure of blood, carrying of ions, fat acids, part of vitamins, pigments and drugs, and supply of amino acids to peripheral tissues. However, albumin is also known to exude to urine in an event of a renal function disorder caused by diabetic nephropathy, one of diabetic complications, and the like.

By measuring the albumin amount in urine, therefore, screening of morbidity, check of the effect of a therapy, determination of prognosis and the like are allowed. For this reason, in recent years, measurement of the albumin amount in urine has become widespread as an important routine test for early detection of diabetic nephropathy and diagnosis of prognosis of diabetes. Measurement of the albumin amount in urine can be executed by an immunological technique using an antibody specifically binding to albumin.

As an antibody against albumin, an anti-human albumin serum as a polyclonal antibody has been conventionally used. In most of conventional albumin measurement methods, albumin is measured by determining whether or not a precipitation line exists, or the turbidity has increased, due to agglutination of the albumin with an antiserum. However, an unpurified antiserum, which often includes various antibodies against various antigens in a serum, may possibly bind to an antigen other than albumin. In the measurement, therefore, to prevent the antiserum from binding to an antigen other than albumin mistakenly, the antiserum is purified, to thereby block occurrence of any reaction derived from an antigen other than albumin in a human standard serum. For purification of an antiserum, a technique such as affinity chromatography is normally used in which an antibody likely to bind to a protein in a human standard serum is removed from the unpurified antiserum.

In the immunoturbidimetry described above, a polyclonal antibody (that is, an antiserum) is used. A polyclonal antibody is generally obtained by purifying a serum collected from blood of an immunized animal. Therefore, although the production method is easy, the properties of the resultant antibody may be highly possibly influenced by the family, environment, physical condition and the like of the immunized animal. For example, in the case of using an anti-human albumin serum, the kind of an anti-human albumin antibody included in an anti-human albumin serum produced may possibly be different (for example, the epitope may be different) from others, and as a result, the reactivity with albumin may vary every time an anti-human albumin serum is produced.

If the reactivity of a polygonal antibody varies every time a new polyclonal antibody is produced, it is difficult to obtain homogeneous antibodies continuously. In this situation, measurement of a subject substance by the immunoturbidimetry may fail to provide repeatable results.

SUMMARY OF THE INVENTION

An object of the present invention is providing an immunoassay method capable of providing highly reliable results in measurement of a specific component in a sample.

The immunoassay method of the present invention is an immunoassay method for measuring the content of a subject substance in a sample. The method includes the steps of: (a) preparing a mixed solution by mixing the sample and an antibody solution including a first monoclonal antibody and a second monoclonal antibody capable of specifically binding to the subject substance; and (b) measuring an optical property of the mixed solution. The first monoclonal antibody is capable of binding to a first epitope of the subject substance, the second monoclonal antibody is capable of binding to a second epitope of the subject substance different from the first epitope, and each of the first epitope and the second epitope exists singly in the subject substance.

A cell strain producing a monoclonal antibody continues producing the same antibody almost permanently. It is therefore possible to provide antibodies invariably uniform in properties and thus suppress a variation in properties among lots of the antibody solution. Thus, according to the present invention, the repeatability of the measurement results of the subject substance is high, and the reliability of the measured values improves.

The optical property may be the intensity of scattered light or the amount of transmitted light.

In the step (a), the half value of inhibition for the first monoclonal antibody and the second monoclonal antibody may be selected from values in a range of $1\times10^{-9}$ M to $1\times10^{-7}$ M.

The mole ratio between the first monoclonal antibody and the second monoclonal antibody in the antibody solution may be changed.

By the above arrangement, the measurable range of the concentration of the subject substance and the detection sensitivity can be changed as required. This enables free design of the measurable range of the concentration of the subject substance and the detection sensitivity.

The subject substance may be albumin.

In the step (a), the antibody solution may further include a third monoclonal antibody, the first monoclonal antibody may be a monoclonal antibody produced from a cell strain under Accession Number FERM BP-7937 of International Patent Organism Depositary, the National Institute of Advanced Industrial Science and Technology, the second monoclonal antibody may be a monoclonal antibody produced from a cell strain under Accession Number FERM BP-7938 of International Patent Organism Depositary, the National Institute of Advanced Industrial Science and Technology, and the third monoclonal antibody may be a monoclonal antibody produced from a cell strain under Accession Number FERM BP-8307 of International Patent Organism Depositary, the National Institute of Advanced Industrial Science and Technology.

In the step (a), the antibody solution may further include a third monoclonal antibody, the first monoclonal antibody may be a monoclonal antibody produced from a cell strain under Accession Number FERM BP-7938 of International Patent Organism Depositary, the National Institute of Advanced Industrial Science and Technology, the second monoclonal antibody may be a monoclonal antibody produced from a cell strain under Accession Number FERM BP-8308 of International Patent Organism Depositary, the National Institute of Advanced Industrial Science and Technology, and the third monoclonal antibody may be a monoclonal antibody produced from a cell strain under Accession Number FERM BP-8309 of International Patent Organism Depositary, the National Institute of Advanced Industrial Science and Technology.

The immunoassay equipment of the present invention is immunoassay equipment for measuring the content of a subject substance in a sample, including: preparation means for preparing a mixed solution by mixing the sample and an antibody solution including a first monoclonal antibody and a second monoclonal antibody capable of specifically binding to the subject substance; and optical measurement means for measuring an optical property of the mixed solution. The first monoclonal antibody is capable of binding to a first epitope of the subject substance, the second monoclonal antibody is capable of binding to a second epitope of the subject substance different from the first epitope, and each of the first epitope and the second epitope exists singly in the subject substance.

The biological component measurable toilet of the present invention is a toilet for measuring the content of a subject substance in excrement, including: excrement collection means for collecting excrement or a mixture of wash water and excrement as a sample; preparation means for preparing a mixed solution by mixing the sample and an antibody solution including a first monoclonal antibody and a second monoclonal antibody capable of specifically binding to the subject substance; and optical measurement means for measuring an optical property of the mixed solution. The first monoclonal antibody is capable of binding to a first epitope of the subject substance, the second monoclonal antibody is capable of binding to a second epitope of the subject substance different from the first epitope, and each of the first epitope and the second epitope exists singly in the subject substance.

An anti-albumin monoclonal antibody of the present invention is produced from a cell strain under Accession Number FERM BP-7938 of International Patent Organism Depositary, the National Institute of Advanced Industrial Science and Technology.

Another anti-albumin monoclonal antibody of the present invention is produced from a cell strain under Accession Number FERM BP-7937 of International Patent Organism Depositary, the National Institute of Advanced Industrial Science and Technology.

Yet another anti-albumin monoclonal antibody of the present invention is produced from a cell strain under Accession Number FERM BP-8307 of International Patent Organism Depositary, the National Institute of Advanced Industrial Science and Technology.

Yet another anti-albumin monoclonal antibody of the present invention is produced from a cell strain under Accession Number FERM BP-8308 of International Patent Organism Depositary, the National Institute of Advanced Industrial Science and Technology.

Yet another anti-albumin monoclonal antibody of the present invention is produced from a cell strain under Accession Number FERM BP-8309 of International Patent Organism Depositary, the National Institute of Advanced Industrial Science and Technology.

A cell strain of the present invention is Accession Number FERM BP-7938 of International Patent Organism Depositary, the National Institute of Advanced Industrial Science and Technology.

Another cell strain of the present invention is Accession Number FERM BP-7937 of International Patent Organism Depositary, the National Institute of Advanced Industrial Science and Technology.

Yet another cell strain of the present invention is Accession Number FERM BP-8307 of International Patent Organism Depositary, the National Institute of Advanced Industrial Science and Technology.

Yet another cell strain of the present invention is Accession Number FERM BP-8308 of International Patent Organism Depositary, the National Institute of Advanced Industrial Science and Technology.

Yet another cell strain of the present invention is Accession Number FERM BP-8309 of International Patent Organism Depositary, the National Institute of Advanced Industrial Science and Technology.

The albumin detection kit of the present invention is a kit for detecting albumin in a sample, including a first monoclonal antibody and a second monoclonal antibody. The first monoclonal antibody is an anti-albumin monoclonal antibody, the second monoclonal antibody is an anti-albumin monoclonal antibody labeled with a labeling substance, and at least one of the first monoclonal antibody and the second monoclonal antibody is an anti-albumin monoclonal antibody produced from a cell strain selected from the group consisting of a cell strain under Accession Number FERM BP-7938 of International Patent Organism Depositary, the National Institute of Advanced Industrial Science and Technology, a cell strain under Accession Number FERM BP-7937 of International Patent Organism Depositary, the National Institute of Advanced Industrial Science and Technology, a cell strain under Accession Number FERM BP-8307 of International Patent Organism Depositary, the National Institute of Advanced Industrial Science and Technology, a cell strain under Accession Number FERM BP-8308 of International Patent Organism Depositary, the National Institute of Advanced Industrial Science and Technology, and a cell strain under Accession Number FERM BP-8309 of International Patent Organism Depositary, the National Institute of Advanced Industrial Science and Technology.

A cell strain producing a monoclonal antibody continues producing the same antibody almost permanently. It is therefore possible to provide monoclonal antibodies invariably uniform in properties and thus suppress a variation in properties among lots of the antibody solution. Thus, in the albumin detection kit of the present invention, the repeatability and reliability of the measurement results of the subject substance improve.

DESCRIPTION OF THE PREFERRED EMBODIMENTS

Hereinafter, preferred embodiments of the present invention will be described with reference to the accompanying drawings.

Embodiment 1

Figure 1:
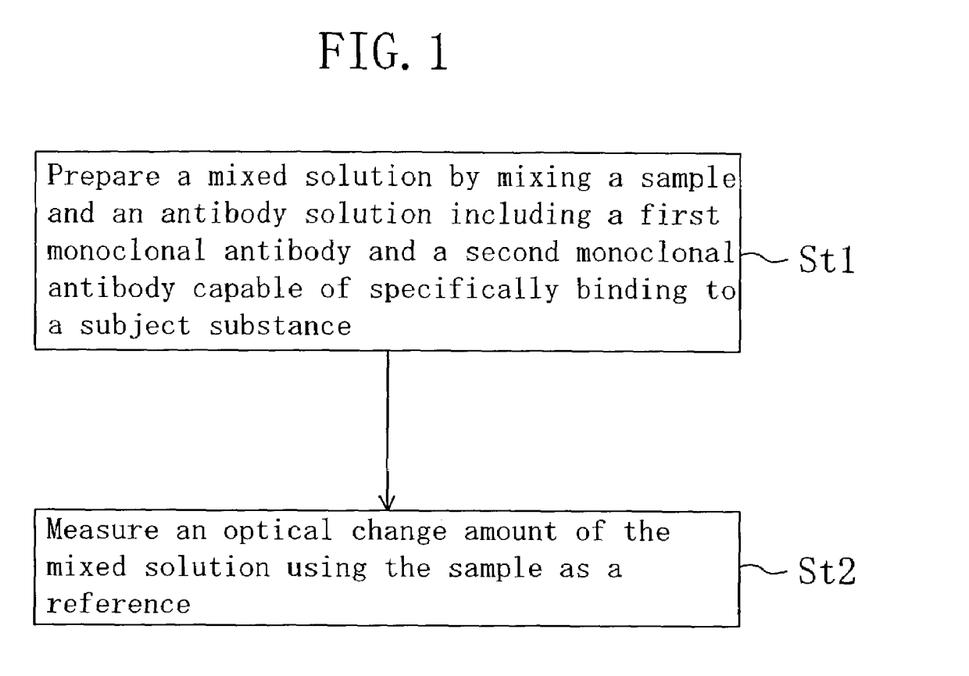
FIG. 1 is a flowchart showing an immunoassay method of the present invention.

FIG. 1 is a flowchart showing an immunoassay method of this embodiment. As used herein, the term "immunoassay method" refers collectively to immunological measurement methods including immunoturbidimetry and immunonephelometry.

As shown in FIG. 1, the immunoassay method of this embodiment, which is an immunoreaction measurement method for measuring the content of a subject substance in a sample, includes step St1 of preparing a mixed solution by mixing a sample and an antibody solution including a first monoclonal antibody and a second monoclonal antibody capable of specifically binding to a subject substance, and step St2 of measuring an optical property of the mixed solution.

Each of the above steps will be described in detail.

In step St1, a sample and an antibody solution are prepared.

Examples of the sample include, but are not limited to, urine, blood, excrement and saliva, for diagnosis of various diseases.

The antibody solution includes a first monoclonal antibody and a second monoclonal antibody that specifically bind to a subject substance. The first monoclonal antibody can bind to a first epitope of the subject substance, and the second monoclonal antibody can bind to a second epitope of the subject substance different from the first epitope. Each of the first and second epitopes exists singly, not at a plurality of positions, in the subject substance.

According to the method described above, if the subject substance is included in the sample, an agglutinated complex is generated due to antigen-antibody reaction between the subject substance and the first and second monoclonal antibodies. In reverse, if the subject substance is not included in the sample, no agglutinated complex is generated due to antigen-antibody reaction between the subject substance and the first and second monoclonal antibodies.

In step St2, an optical property of the mixed solution is measured. If an agglutinated complex has been generated, the reaction system becomes turbid causing a change in the intensity of scattered light, the amount of transmitted light and the like. Therefore, by measuring the intensity of scattered light, the amount of transmitted light or the like, the degree of turbidity of the mixed solution can be estimated. In this measurement, a reference solution, obtained by excluding the specifically binding substance from the above reaction system, may preferably be used as the reference, to measure the optical change amount in the reaction system, that is, the change amount in the intensity of scattered light, the amount of transmitted light or the like. Otherwise, a reference solution obtained by excluding the sample from the reaction system may be used. The optical property of the mixed solution may be the intensity of scattered light or the amount of transmitted light. In the immunoturbidimetry, the intensity of scattered light in the mixed solution is measured, while in the immunonephelometry, the amount of transmitted light is measured.

In general, a polyclonal antibody is obtained in the following manner. A large-size animal such as goat and a rabbit is immunized. After it is confirmed that the antibody titer and the affinity have been saturated, a serum of the animal is collected several times over several months, and the collected serum is purified. Therefore, even a polyclonal antibody having an affinity below saturation, not to mention a polyclonal antibody having an affinity above saturation, finds difficulty in maintaining the quality. Accordingly, in the conventional method using a polyclonal antibody, the quality of the antibody solution varies, and the repeatability of the measurement results and the reliability of the measured value degrade.

On the contrary, a cell strain producing a monoclonal antibody continues producing the same antibody almost permanently. It is therefore possible to provide antibodies invariably uniform in properties and thus suppress a variation in properties among lots of the antibody solution. Accordingly, in this embodiment, the repeatability of the measurement results of the subject substance is high, and the reliability of the measured values improves.

In addition, each of the first and second epitopes exists singly, not at a plurality of positions, in the subject substance. Therefore, with only one kind of monoclonal antibody, formation of an agglutinated complex due to antigen-antibody reaction is hardly possible although this formation is indispensable for the immunoassay method. In this embodiment, two kinds of monoclonal antibodies capable of binding to different epitopes of the subject substance are mixed together to prepare the antibody solution. Naturally, three or more kinds of monoclonal antibodies capable of binding to different epitopes of the subject substance may be mixed together to prepare the antibody solution. Considering the cost in production of the antibody solution, the number of kinds of monoclonal antibodies included in the antibody solution is preferably 20 or less.

The half value of inhibition for the monoclonal antibodies used in the immunoassay method of this embodiment is preferably selected from those in the range of $1 \times 10^{-11}$ M to $1 \times 10^{-5}$.

The "half value of inhibition" as used herein is defined as follows in an inhibition ELISA method. That is, when the amount of a monoclonal antibody binding to a subject substance immobilized to a solid phase decreases due to addition of a competitor substance (inhibitor; herein identical to the subject substance) compared with the amount under absence of the inhibitor, the concentration of the inhibitor at which the absorbance (reflecting the antibody binding amount) measured is a half of that obtained under absence of the inhibitor is called the "half value of inhibition".

In the case of using an antibody solution including three or more kinds of monoclonal antibodies different in epitope and affinity in the subject substance, an antigen-antibody complex is formed from complicate intertwining of epitopes and affinities of the monoclonal antibodies. In this case, the size and concentration of the agglutinated complex vary with the mole ratio among the monoclonal antibodies. Therefore, using this feature, it is possible to change the measurable range of the concentration of the subject substance and the detection sensitivity as required. In this way, free design of the measurable range of the concentration of the subject substance and the detection sensitivity is allowed.

To state specifically, human albumin may be measured using an antibody solution prepared by mixing the following anti-human albumin monoclonal antibodies: a monoclonal antibody produced from a cell strain under Accession Number FERM BP-7938 of International Patent Organism Depositary (IPOD), the National Institute of Advanced Industrial Science and Technology (AIST) (hereinafter, called 7938 strain); a monoclonal antibody produced from a cell strain under AIST IPOD Accession Number FERM BP-8308 (hereinafter, called 8308 strain); and a monoclonal antibody produced from a cell strain under AIST IPOD Accession Number FERM BP-8309 (hereinafter, called 8309 strain). By changing the mole ratio among the monoclonal antibodies of this antibody solution, the sensitivity can be changed when the albumin concentration of a human serum is low.

The half value of the albumin concentration (half value of inhibition) inhibiting binding of the antibodies described above to human serum albumin applied to an ELISA plate at $1 \times 10^{-7}$ M is $3.0 \times 10^{-9}$ M for the monoclonal antibody derived from the 7938 strain (hereinafter, called 7938 antibody), $3.2 \times 10^{-10}$ M for the monoclonal antibody derived from the 8308 strain (hereinafter, called 8308 antibody), and $1.0 \times 10^{-9}$ M for the monoclonal antibody derived from the 8309 strain (hereinafter, called 8309 antibody).

In the case of mixing three or more kinds of monoclonal antibodies different in affinity, control of the prozone phenomenon will be easier if monoclonal antibodies different greatly in affinity from one another are used.

To state specifically, human serum albumin may be measured using an antibody solution prepared by mixing the following anti-human albumin monoclonal antibodies: a monoclonal antibody produced from the cell strain under AIST IPOD Accession Number FERM BP-7938 (hereinafter, called 7938 strain); a monoclonal antibody produced from a cell strain under AIST IPOD Accession Number FERM BP-7937 (hereinafter, called 7937 strain); and a monoclonal antibody produced from a cell strain under AIST IPOD Accession Number FERM BP-8307 (hereinafter, called 8307 strain). By changing the mole ratio among the monoclonal antibodies of this antibody solution, it is possible to change the albumin concentration of a human serum at which the prozone phenomenon occurs in the range of 10 mg/dl to 50 mg/dl.

The half value of the albumin concentration (half value of inhibition) inhibiting binding of the antibodies described above to human serum albumin applied to an ELISA plate at $1 \times 10^{-7}$ M is $3.0 \times 10^{-9}$ M for the monoclonal antibody derived from the 7938 strain (hereinafter, called 7938 antibody), $5.5 \times 10^{-7}$ M for the monoclonal antibody derived from the 7937 strain (hereinafter, called 7937 antibody), and $7.0 \times 10^{-8}$ M for the monoclonal antibody derived from the 8307 strain (hereinafter, called 8307 antibody).

The "anti-albumin monoclonal antibody" of the present invention also includes its fragments retaining the binding property of the antibody. These fragments can compete with intact antibody from which these fragments are derived on the specific binding to albumin, and can bind to albumin with an affinity of at least $1 \times 10^7$ to $1 \times 10^{10}$ $M^{-1}$. The antibody fragments may include heavy chains, light chains, Fab, Fab', F(ab')$_2$, Fabc and Fv of immunoglobulin, and can be generated by enzymatic or chemical separation of intact immunoglobulin. For example, F(ab')$_2$ fragment can be obtained from IgG molecule by protein digestion with pepsin under pH 3.0 to 3.5 using a standard method as that described in Harlow and Lane, Antibodies: A Laboratory Manual, Cold Spring Harbor Laboratory, New York (1988). Fab fragment can be obtained from the F(ab')$_2$ fragment by limited reduction, or from the entire antibody by papain digestion under the presence of a reducing agent (see W Paul (Ed.), Fundamental Immunology, 2nd Ed., Ravan Press, N.Y., 1989, Chapter 7).

Figure 2:
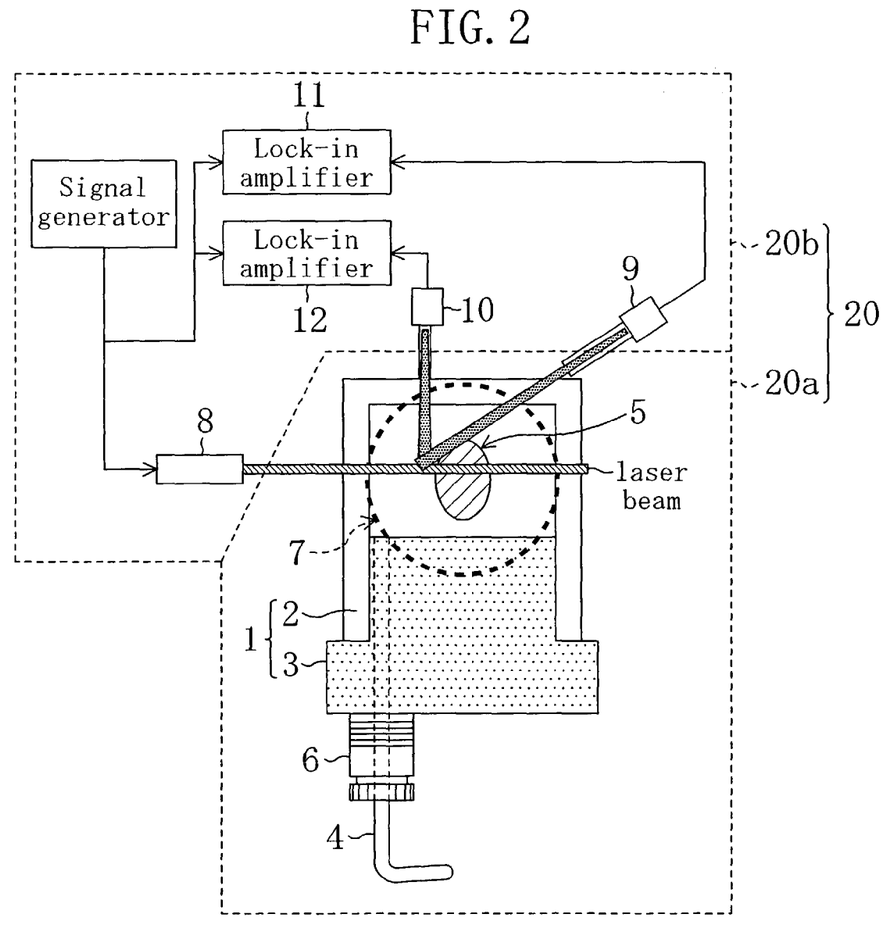
FIG. 2 is a schematic top view of measurement equipment used for the immunoassay method of the present invention.

FIG. 2 is a schematic top view of measurement equipment 20 used for the immunoassay method of this embodiment.

The measurement equipment 20 includes: a preparation means 20a for preparing a mixed solution by mixing a sample and an antibody solution including a first monoclonal antibody and a second monoclonal antibody capable of specifically binding to a subject substance; and an optical measurement means 20b for measuring an optical property of the mixed solution. The first monoclonal antibody is capable of binding to a first epitope of the subject substance, and the second monoclonal antibody is capable of binding to a second epitope of the subject substance different from the first epitope. Each of the first and second epitopes exists singly in the subject substance.

In this embodiment, as shown in FIG. 2, the preparation means 20a includes a sample cell 1 composed of a fixed base 2 and a sample base 3, a tube 4 for injecting an antibody solution, connected to the sample base 3 via a tubing connector 6, and an agitator 5 placed in the sample cell 1.

A microstirrer 7 is embedded in the fixed base 2, to enable the agitator 5 placed in the sample cell 1 to rotate. The sample base 3 is secured on the fixed base 2 to form the sample cell 1 (light path length: 10 mm) capable of retaining a liquid. An antibody solution is injected into the sample cell 1 through the tube 4 via the tubing connector 6.

The optical measurement means 20b includes: a semiconductor laser module 8; and photodiode arrays 9 and 10 positioned to be able to detect 45-degree forward scattered light (Sc45) and 90-degree sideways scattered light (Sc90) of a laser beam (wavelength: 680 nm, power: 15 mW, beam diameter: about 1.2 mm) emitted from the semiconductor laser module 8 toward the sample cell 1.

In this embodiment, to improve the detection sensitivity of the scattered light, the laser beam is pulse-modulated with a frequency of 270 Hz, and signals output from the photodiodes 9 and 10 detecting the scattered light are phase-sensitive detected with lock-in amplifiers 11 and 12, respectively. Signals output from the lock-in amplifiers 11 and 12 can be detected as signals corresponding to the respective scattered light intensities.

Embodiment 2

With the recent health-minded tendency, there has grown a need for real-time check of heath condition at home. To satisfy this need, it is requested that a health-indicator substance in a fluid such as urine and blood can be measured in one step in such a measurable range and with such a sensitivity that are appropriate for the need.

In this embodiment, a biological component measurable toilet permitting real-time check of health condition at home will be described with reference to FIG. 3.

Figure 3:
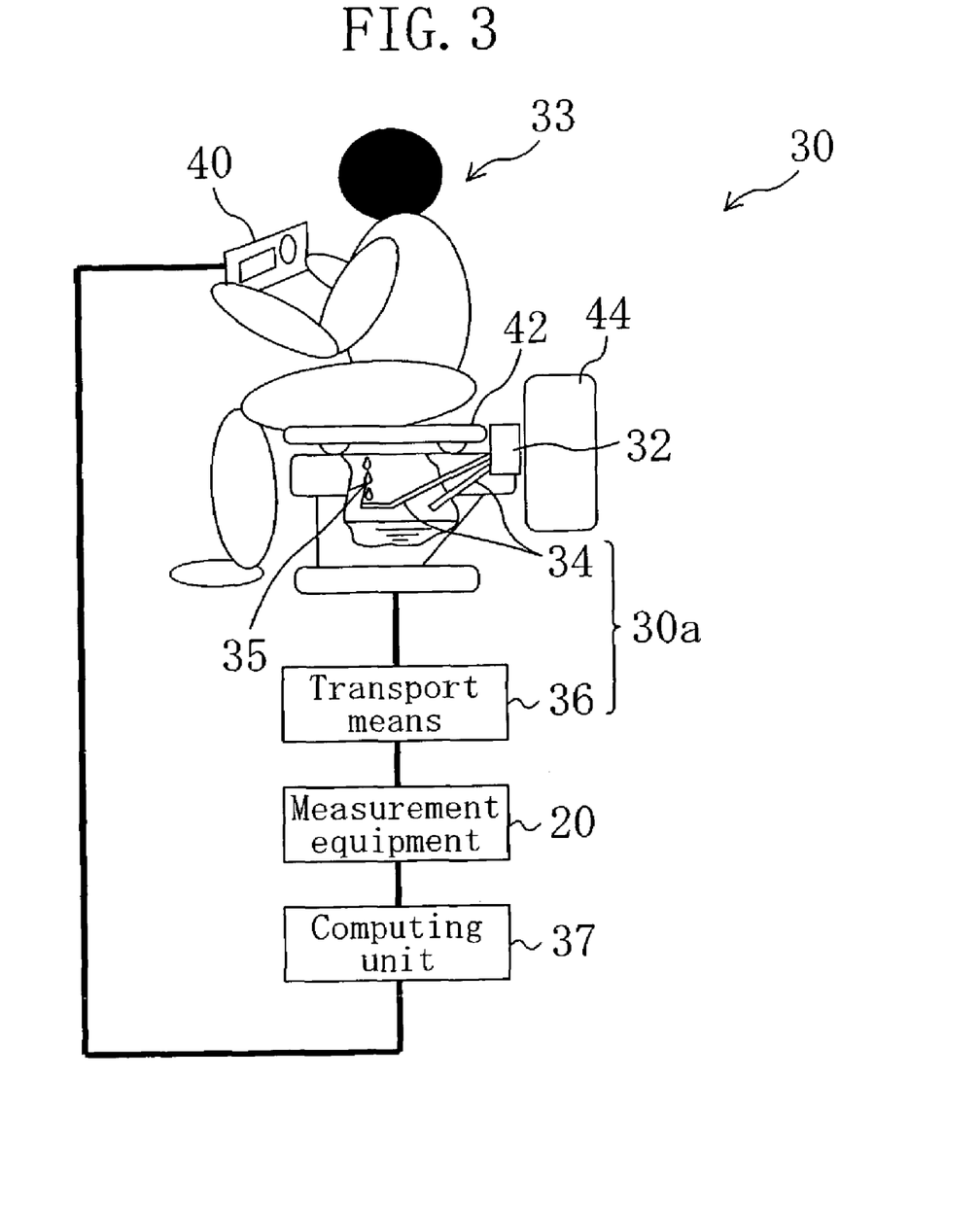
FIG. 3 is a diagrammatic view of a biological component measurable toilet of the present invention.

Referring to FIG. 3, a biological component measurable toilet 30 of this embodiment, for measuring the content of a subject substance in excrement (urine, fecal matter and the like), includes: an excrement collection means 30a for collecting excrement or a mixture of wash water and excrement as a sample; and the measurement equipment 20 described in Embodiment 1.

In this embodiment, the excrement collection means 30a includes a wash nozzle 31 through which wash water is supplied, an excrement holding means 34 for holding excrement (fecal matter or urine) 35 egested from a user 3 washed with and included in the wash water supplied from the wash nozzle 31, and a transport means 36 for transporting the excrement 35 from the excrement holding means 34 holding the excrement 35 to the sample cell of the measurement equipment 20.

In this embodiment, a computing unit 37 is also provided for computing the concentration of the subject substance in the excrement from the output of the measurement equipment 20.

The toilet of this embodiment also includes a display means 40 equipped with a remote controller and a communication means for displaying the concentration of a biological component sent from the computing unit 37 and the like, a seat 42, a bowl 43 and a tank 44. In the example illustrated in FIG. 3, the user 33 sits on the seat 42 to urinate.

As an example of the operation, measurement of albumin included in urine using the biological component measurable toilet of this embodiment will be described.

The excrement 35 from the user 33 is held on the excrement holding means 34 placed to receive the dropping excrement, and transported to the sample cell 1 of the measurement equipment 20 by the transportation means 36. Albumin in the excrement 35 is measured by the measurement equipment 20 in which a mixed solution of the anti-human albumin monoclonal antibodies (mole ratio among the mixed antibodies, 7937 antibody, 7938 antibody and 8307 antibody is 4:3:3) has been set in advance. The measured value is converted to a concentration based on a calibration curve stored in advance in the computing unit 37, and the converted concentration is displayed on the display means 40.

The albumin concentration received by the display means 40 may be transferred to a medical facility that administers health information on the user 33, such as a health care center, via the communication means. In the medical facility, a health advice and the like may be prepared based on the received data and sent to the user 33. Furthermore, under contract between the user 33 and the medical facility or the like, meals, consumables, service and the like fit for the health condition of the user 33 may be delivered to the user 33 under administration of the medical facility or the like.

Embodiment 3

In this embodiment, an albumin detection kit using the monoclonal antibodies used in Embodiment 1 will be described.

The albumin detection kit of this embodiment, for detecting albumin in a sample, includes a first monoclonal antibody and a second monoclonal antibody. The first monoclonal antibody is an anti-albumin monoclonal antibody, and the second monoclonal antibody is an anti-albumin monoclonal antibody labeled with a labeling substance by a method known in the art. Examples of the labeling substance include an enzyme, a pigment, a magnetic substance, a radioactive substance and colored particles (gold colloid, latex and the like).

At least either of the first monoclonal antibody and the second monoclonal antibody is an anti-albumin monoclonal antibody produced from a cell strain selected from the group consisting of the cell strain under AIST IPOD Accession Number FERM BP-7938, the cell strain under AIST IPOD Accession Number FERM BP-7937, the cell strain under AIST IPOD Accession Number FERM BP-8307, the cell strain under AIST IPOD Accession Number FERM BP-8308 and the cell strain under AIST IPOD Accession Number FERM BP-8309.

Some of the cell strains described above produce a monoclonal antibody having a high binding ability to albumin. A typical anti-albumin monoclonal antibody is a monoclonal antibody produced from the cell strain under Accession Number FERM BP-7938 (7938 antibody). The binding ability of such a monoclonal antibody to albumin gives inhibition in measurement under substantially the same conditions as those in the inhibition ELISA method to be described later in Examples, and the half value of inhibition may be about $1 \times 10^{-8}$ M or less. By using a monoclonal antibody giving a half value of inhibition as described above for the albumin detection kit of this embodiment, albumin in a solution can be detected with high sensitivity. Moreover, since albumin in a concentration conventionally undetectable can be measured, the detection kit of this embodiment may serve as an effective means for obtaining new findings in the clinical field. The "solution" as used herein may include fluid such as urine and blood, but is not limited to these.

In general, it is known that albumin can be measured when its concentration in a solution is in the range of about 0.05 to about 5.0 mg/L at highest. According to the present invention, however, by using the 7938 antibody for the albumin detection kit of this embodiment, for example, it is possible to provide a sensitivity permitting detection of albumin having a concentration in the range of about 0.0066 to 0.66 mg/L in a solution.

Some of the cell strains described above produce a monoclonal antibody that permits quantification of albumin having a concentration exceeding the range of about 30 to 300 mg/L when the monoclonal antibody is used for the albumin detection kit of this embodiment. A typical anti-albumin monoclonal antibody is a monoclonal antibody produced from the cell strain under AIST IPOD Accession Number FERM BP-7937 (7937 antibody). The binding ability of such a monoclonal antibody to albumin gives inhibition in measurement under substantially the same conditions as those in the inhibition ELISA method to be described later in Examples, and the half value of inhibition is about $1 \times 10^{-7}$ M to about $1 \times 10^{-5}$ M. In particular, the half value of inhibition for a monoclonal antibody is preferably around $1 \times 10^{-6}$ M, more preferably about $1 \times 10^{-6.3}$ M. By using an monoclonal antibody having a half value of inhibition as described above, it is possible to measure albumin having a concentration exceeding the range of about 30 to about 300 mg/L in a solution.

In general, it is known that the measurable range of the albumin concentration in a solution is 30 to 300 mg/L. According to the present invention, however, by using the 7937 antibody for the albumin detection kit of this embodiment, for example, it is possible to quantify albumin in a concentration of about 6.6 to about 660 mg/L in a solution. Accordingly, during measurement of the albumin concentration in urine in a test of diabetic nephropathy, it is possible to fully measure a concentration that is in the border region between early nephrophathy and manifest nephrophathy. Therefore, the detection kit of this embodiment may serve as an effective means for obtaining new findings in the clinical field. Only one kind of such a monoclonal antibody having a half value of inhibition as described can cover the measurable range of the albumin concentration broadly. Therefore, the cost required for albumin measurement can be reduced.

The albumin detection kit of this embodiment adopts an immunological technique known in the art. Examples of such an immunological technique include ELISA, RIA and a fluorescent antibody technique.

ELISA and other techniques using a highly sensitive antibody are used for high-sensitivity detection of albumin. In particular, for ELISA, a high-affinity anti-albumin antibody is necessary. However, it is difficult to maintain the quality of an anti-albumin antiserum constant independent of the physical condition of an immunized animal and the environment surrounding the animal.

A cell strain producing a monoclonal antibody continues producing the same antibody almost permanently. It is therefore possible to provide antibodies invariably uniform in properties and thus suppress a variation in properties among lots of the kit. Accordingly, in this embodiment, the repeatability and reliability of the detection results of a subject substance improve.

EXAMPLES

Hereinafter, the present invention will be described in more detail in the form of specific examples. Note however that the present invention is not limited to these examples. In the following examples, "ALB" refers to albumin.

Example 1

Figure 4:
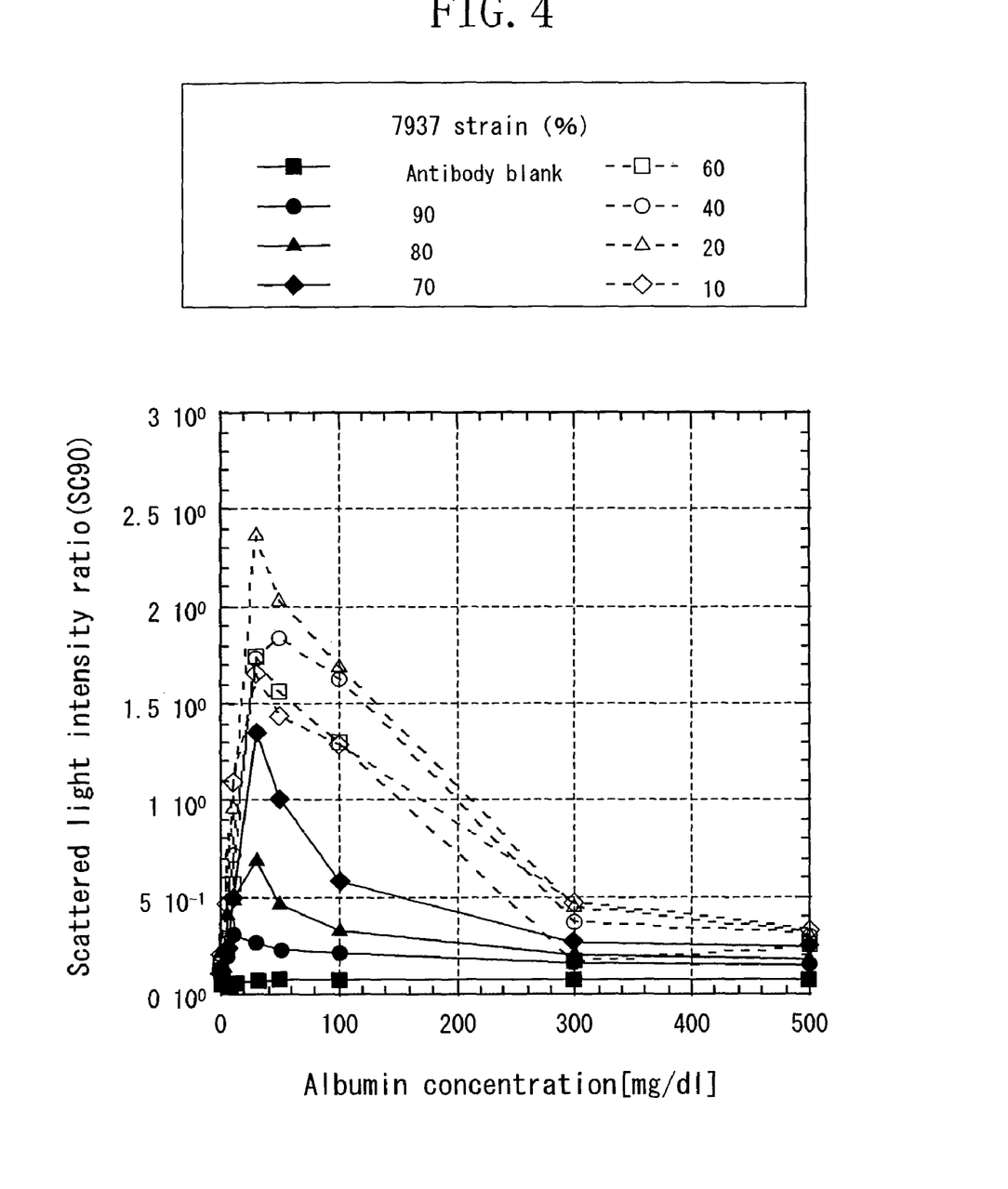
FIG. 4 is a graph showing the turbidity with respect to the concentration of a subject substance (human albumin), examined for antibody solutions obtained by mixing three kinds of monoclonal antibodies at different mole ratios.

Using the measurement equipment 20 of FIG. 2 described in Embodiment 1, 9 μl of a hSA (human serum albumin) solution as an antigen was injected into the sample cell 1 while being stirred, and then 145 μl of a 50 mM succinic acid buffer (pH: 5.0, containing 5% PEG6000) was injected into the sample cell 1. After the lapse of 30 seconds or more, measurement was started. After 10 seconds, 40 μl of an antibody solution was injected into the sample cell 1, and after 20 seconds, the stirrer was stopped. The turbidity of the solution in the cell was measured until 300 seconds from the start. As the antibody solution, the 7937 strain, the 8307 strain and the 7938 strain of the antigen solution were mixed at ratios of 90:5:5, 80:10:10, 70:15:15, 60:20:20, 40:30:30, 20:40:40 and 10:45:45 while the antibody concentration of the antibody solution was kept at 0.1 mg/ml. The antigen was prepared to provide final concentrations of 0.5, 10, 30, 50, 100, 300 and 500 (mg/dl), to perform measurement at seven types of antigen concentrations for each of the antibody solutions of different mole ratios. The results are shown in FIG. 4.

For the antibody solution including the 7937 strain at 90%, the prozone started at 10 mg/dl. For the antibody solution including the 7937 strain at 40%, the turbidity rose with increase of the albumin concentration until 50 mg/dl. For the antibody solution including the 7937 strain at 20%, the turbidity rose until 30 mg/dl. It was therefore found that the sensitivity was very high in the low concentration range. From these results, it is indicated that the measurable range and the sensitivity can be controlled by changing the mixing mole ratio among a plurality of monoclonal antibodies different in affinity.

Example 2

Figure 5:
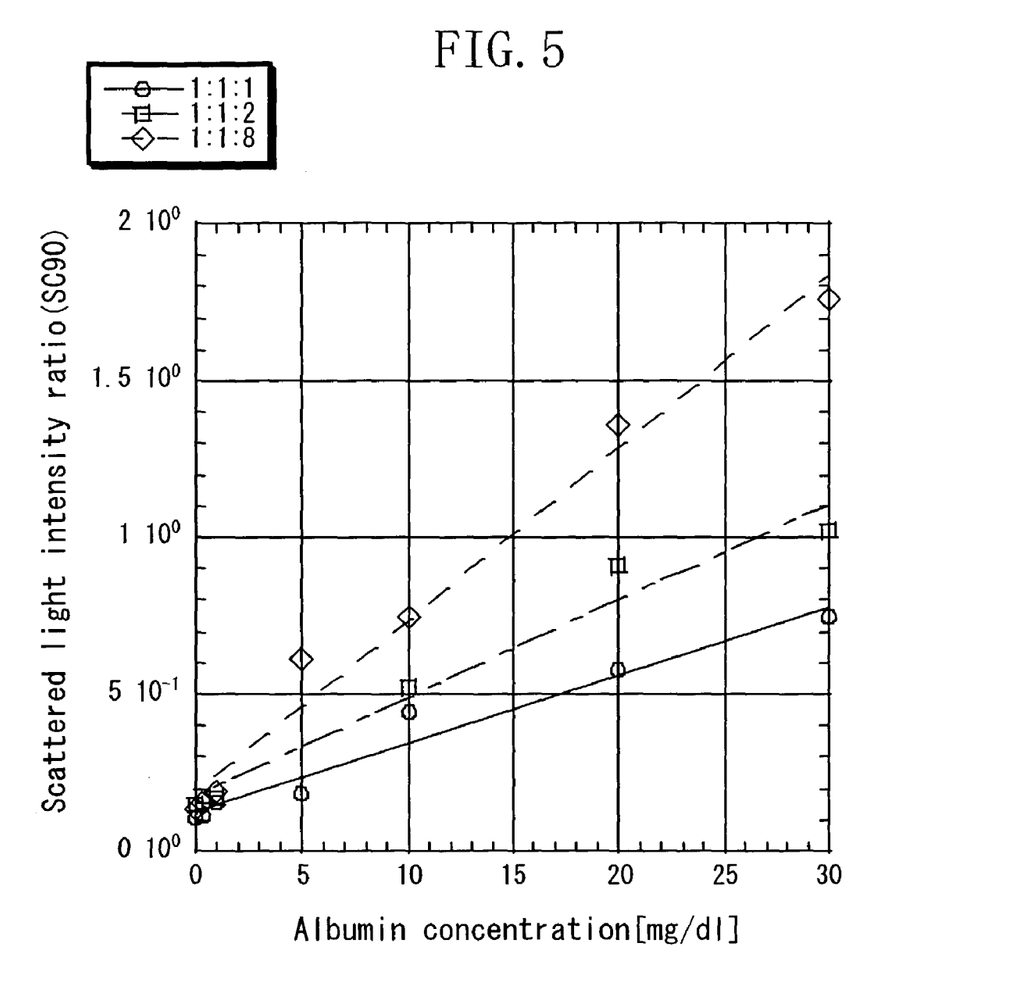
FIG. 5 is a graph showing the turbidity with respect to the concentration of a subject substance (human albumin), examined for antibody solutions obtained by mixing three kinds of monoclonal antibodies at different mole ratios.

Three types of antibody solutions were prepared by mixing the 8308 antibody, the 8309 antibody and the 7937 antibody at mole ratios of 1:1:1, 1:1:2 and 1:1:8 while the concentration of the mixed antibodies was kept at 0.3 mg/ml. The antigen was prepared to provide a final concentration of 0 to 30 mg/dl. The immunoturbidimetry was performed using the mixed antibody solutions of the above mole ratios under the conditions described in Example 1. The results are shown in FIG. 5. It is found from FIG. 5 that up to the albumin concentration of 30 mg/dl, the sensitivity can be enhanced by increasing the mole fraction of the 7937 antibody.

Example 3

<Enzyme-Linked Immunosorbent Assay (ELISA)>

In this example, an antiserum, a culture supernatant and a monoclonal antibody obtained were evaluated by an ELISA method. The procedure of this method is as follows.

(A) Coating of Antigen (ALB)

An ALB solution was prepared at a concentration of $1 \times 10^{-7}$ M using a 0.04 wt. % sodium azide PBS (PBS-Az) solution. This ALB solution, 100 μl/well, was applied to a microplate (polystyrene, high binding, flat-bottomed, #2580 of Costar), and the resultant microplate was allowed to stand overnight in saturated water vapor at room temperature. The ALB solution was removed with an aspirator immediately before an experiment.

(B) Blocking

A 1 wt % casein PBS-Az solution, 200 µl/well, was applied to the microplate, and the resultant microplate was allowed to stand for 30 minutes. The 1 wt % casein PBS-Az solution was then removed with an aspirator. The resultant microplate is stored in saturated water vapor at room temperature if the subsequent experiment is not performed on the same day.

(C) Reaction of Antibody

An antibody solution (antiserum, culture supernatant, purified antibody, and the like) diluted with the 1 wt % casein PBS-Az solution to various concentrations, 50 µl/well, and the 1 wt % casein PBS-Az solution, 50 µl/well, were applied to the microplate. When an inhibition experiment is performed for the purpose of measuring relative affinity, 50 µl/well of an inhibitor solution (solution including ALB) was applied, then 50 µl/well of the antibody solution was added, and the resultant microplate was shaken. After allowing to stand at room temperature for one and a half hours, the microplate was washed with PBS three times, and the remaining PBS was removed with an aspirator.

(D) Reaction of Labeled Antibody

A solution obtained by dissolving 0.2 µg/ml peroxidase-labeled goat-derived anti-mouse IgG antibody (KPL) in a 1 wt. % casein PBS solution, or a solution obtained by dissolving 0.2 µg/ml peroxidase-labeled goat-derived anti-mouse IgM antibody (KPL) in a 1 wt. % casein PBS solution, 100 µl/well, was applied to the microplate, and the resultant microplate was allowed to stand for 30 minutes at room temperature. The microplate was washed with PBS three times, and the remaining PBS was removed with an aspirator.

(E) Reaction of Substrate and Stop of Reaction

A solution (substrate solution) obtained by dissolving 40 mg O-phenylenediamine (for biochemical use) in 10 ml of a citric acid-phosphoric acid buffer (pH 5) and adding 40 µL of 30 wt. % oxygenated water immediately before use, 100 µl/well, was applied to the microplate, and the resultant microplate was allowed to stand at room temperature. After about 2 minutes, 25 µl/well of 4N sulfuric acid was applied to the microplate, and then the reaction was stopped.

(F) Measurement

The absorbance for a wavelength of 492 nm was measured with a microplate reader (Tosoh Corp.). The results obtained indicated correlation between the concentration of the inhibitor and the binding rate (%) to a solid-phase antigen. The binding rate (%) to a solid-phase antigen can be obtained as a relative value (%) of absorbance.

In this example, the ELISA technique was used as an immunoassay method. Alternatively, RIA, the fluorescent antibody technique and the like may be employed.

Example 4

In this example, an A/J strain mouse was used for immunization considering the experiences of using this animal in the laboratory to which the present inventors belong.

(Immunization)

A solution of 2 mg/ml albumin (ALB) (Sigma Inc.) as an immunogen was prepared using phosphate buffered saline (PBS). An adjuvant (complete Freund's adjuvant containing human killed tubercle bacilli, H37Rv of Wako Pure Chemical Industries, Ltd.) of the same volume was added to the ALB PBS solution. The resultant solution was sufficiently emulsified with a homogenizer at 1000 rpm, to obtain an immunogen-containing adjuvant emulsion.

Each 100 µl of the immunogen-containing adjuvant emulsion was injected into 5 male mice (A/J) of about 7 weeks old intra-abdominally or hypodermically. After 3 weeks, a 2 mg/ml ALB solution prepared using PBS and an incomplete Freund's adjuvant of the same volume were emulsified with a homogenizer, and each 100 µl of the resultant emulsion was injected into the same sites of the A/J mice as in the previous injection.

Thereafter, 4, 6 and 12 weeks after the start of the immunization, each 100 µl of the incomplete Freund's adjuvant including ALB of the same composition and concentration as those in the immunization after 3 weeks was injected into the same sites of the mice. Blood was collected 1 week after each of the second, third and fourth injections, to check production of an antibody in the following manner.

(Check of Antibody Production)

A serum was separated from the collected blood, and the serum obtained was examined to check production of an antibody by the ELISA method. In this method, the microplate coated with 100 µl/well of $1 \times 10^{-7}$ M ALB and allowed to stand overnight at room temperature was used. As the second antibody, a peroxydase-labeled anti-mouse IgG antibody or a peroxydase-labeled anti-mouse IgM antibody was used. Existence of an antibody binding to the ALB in the antibody sample is confirmed if coloring is observed in the wells.

As a result of the above check, production of an anti-ALB antibody was recognized in all of the five mice. Moreover, it was confirmed for all the mice that the antibody production had shifted from IgG to IgM after the second injection and that the IgG/IgM ratio was 100 or more after the third injection, indicating that class switching had occurred satisfactorily.

(Cell Fusion)

Final immunization was performed to enlarge the spleens of 3 mice exhibiting the highest titers among the immunized mice. Ten weeks after the start of the immunization, a solution of 1 mg/ml ALB as an immunogen was prepared using PBS, and each 100 µl of the solution without addition of an adjuvant was injected into the mice.

Three days after the final immunization, spleen cells of one of the mice were taken out. The spleen cells were fused with a mouse myeloma-derived cell strain (P3X63-Ag8.653) to obtain fused cells.

The fused cells were allowed to float in a hypoxanthine/aminopterin/thymidine (HAT) medium prepared from Isikov medium containing a 15 wt % fetal cow serum (FCS), and then poured to one 96-well plate (200 µl/well). As feeder cells (cells supplying a growth factor at the start of a culture), spleen cells of the same mouse individual were used. The culture was started in a $CO_2$ incubator ($CO_2$ concentration: 5 vol. %, temperature: 37° C., humidity: 95%). These conditions were also adopted in cultures to follow unless otherwise specified.

(Cell Screening and Cloning)

After 10 days, 100 µl of a culture supernatant of the fused cells was collected. The remaining cultured liquid including the fused cells was poured to four 24-well plates for subculture, and a hypoxanthine/thymidine (HT) medium containing 1 ml of 15 wt. % FCS was added to each well.

Four days after the subculture of the fused cells on the 24-well plates, 150 µl/well of a cell culture supernatant was collected. Using the collected culture supernatant and a culture supernatant collected one week after the start of the culture, the binding ability to ALB was measured by the ELISA method as follows.

As the solid phase, 100 μl/well of a solution of ALB prepared using PBS-Az to have a concentration of $1\times10^{-7}$ M was used. As the antibody liquid, the cell culture supernatant was used. As the second antibody, a peroxydase-labeled anti-mouse IgG antibody was used.

From the ELISA results of the culture supernatants collected at two different times, 30 wells were determined as having high binding ability to ALB and exhibiting good growth as first-stage selection. Cells in these wells were subcultured on five 6-well plates, and 4 ml of a HT medium containing 15 wt. % FCS was added to each well.

Two days after the first-stage cell screening, a culture supernatant was collected, and the binding ability to ALB was measured by the following ELISA method (inhibition ELISA method).

As the solid phase, 100 μl/well of a solution of ALB prepared using PBS-Az to have a concentration of $1\times10^{-7}$ M was used, and ALB was used as the inhibitor. As the antibody liquid, the cell culture supernatant was used. As the labeled antibody, a peroxydase-labeled anti-mouse IgG antibody was used. If an antibody binding to ALB exists in the cell culture supernatant, the antibody binds to the soluble ALB added as the inhibitor, causing inhibition (that is, binding of the antibody to the solid-phase ALB is inhibited). Therefore, no coloring is exhibited in the wells.

Therefore, as the second-stage selection, selected were 5 wells having high binding ability to ALB and thus causing inhibition in the inhibition ELISA method. Cells in the selected wells were subcultured in intermediate flasks (volume: 50 ml), and 45 ml of a HT medium containing 15 wt. % FCS was added to each flask.

Three days after the subculture of the cells selected in the second-stage selection, a culture supernatant was collected, and the binding ability to ALB was measured by the following ELISA method.

As the solid phase, 100 μl/well of a solution of ALB prepared using PBS-Az to have a concentration of $1\times10^{-7}$ M was used, and ALB was used as the inhibitor. As the antibody liquid, the cell culture supernatant was used. As the second antibody, a peroxydase-labeled anti-mouse IgG antibody was used. Inhibition occurs if an antibody binding to the inhibitor exists in the cell culture supernatant. Therefore, no coloring is exhibited in each well. Therefore, 13 wells that had caused inhibition only for ALB were selected.

Cloning was performed for cells in the selected 13 wells in a total of four times, The solution in each well was diluted using a HT medium containing 15 wt. % FCS to a concentration of one cell per well (limit dilution), and the diluted solution was distributed to 13 96-well microplates. Initial growth was promoted with thymocyte cells of 4-week-old female mice (A/J) as the feeder. The culture was continued using plates having gradually increasing sizes. At appropriate occasions, screening of a cell culture supernatant by the ELISA method described above was repeated. A cell strain that had a high titer for ALB and also exhibited good growth was finally selected, and the selected cell strain was cultured until the concentration reaches $5'10^5$ cells/ml in 200 ml of a medium.

One strain that had high binding ability to ALB was finally selected. This cell strain was named 13-3B and deposited with International Patent Organism Depositary, the National Institute of Advanced Industrial Science and Technology on Mar. 7, 2002 (Accession Number FERM BP-7938). Herein, an antibody produced from the 13-3B strain (7938 strain) is called 7938 antibody.

Also, one strain that had a binding ability to ALB causing a change in the degree of binding to the solid-phase albumin when the ALB concentration is in the range of $1\times10^{-7}$ M to $1\times10^{-5}$ M was finally selected. This cell strain was named 11-4B and deposited with International Patent Organism Depositary, the National Institute of Advanced Industrial Science and Technology on Mar. 7, 2002 (Accession Number FERM BP-7937). Herein, an antibody produced from the 11-4B strain (7937 strain) is called 7937 antibody.

Also, three strains that had binding ability to ALB causing a change in the degree of binding to the solid-phase albumin when the ALB concentration is in the range of $1\times10^{-10}$ M to $1\times10^{-7}$ M (that is, strains in which the half value of inhibition is in the range of $1\times10^{-10}$ M to $1\times10^{-7}$ M) were finally selected. These cell strains were named 42DB1, 56E'61 and 56FT4. The 42DB1 strain was deposited with International Patent Organism Depositary, the National Institute of Advanced Industrial Science and Technology on Feb. 27, 2003 (Accession Number FERM BP-8307). Herein, an antibody produced from the 42DB1 strain (8307 strain) is called 8307 antibody. The 56E'61 strain was deposited with International Patent Organism Depositary, the National Institute of Advanced Industrial Science and Technology on Feb. 27, 2003 (Accession Number FERM BP-8308). Herein, an antibody produced from the 56E'61 strain (8308 strain) is called 8308 antibody. The 56FT4 strain was deposited with International Patent Organism Depositary, the National Institute of Advanced Industrial Science and Technology on Feb. 27, 2003 (Accession Number FERM BP-8309). Herein, an antibody produced from the 56FT4 strain (8309 strain) is called 8309 antibody.

(Preservation of Cells)

The finally selected cell strains were centrifuged to remove the supernatant, and allowed to float in 1 ml of a solution of FCS: dimethylsulfoxide of 9:1 (volume ratio) at a concentration of $1\times10^7$ cells/ml. The resultant solution was preliminarily frozen at −80° C., and then stored in a liquid nitrogen environment for long preservation.

(Purification of Antibody)

Each of the selected strains was cultured in large quality with Isikov medium containing 15 wt. % FCS, and the resultant culture was centrifuged to obtain a culture supernatant. The culture supernatant was subjected to affinity chromatography using protein A binding gel (Protein A Cephalose 4FF of Pharmacia), to purify the monoclonal antibody (7938 antibody and 7937 antibody) under the following conditions.

A column filled with protein A binding gel was equilibrated with a binding buffer (1.5 M glycine and 3M NaCl, pH 8.9). The culture supernatant or ascites was diluted about three-fold with the binding buffer, and the diluted solution was applied to the equilibrated column. While an eluate from the column was monitored at 280 nm, the column was washed with the binding buffer until elution of an impurity was terminated. After the washing, an elution buffer (100 mM citric acid, pH 4) was applied to the column (linear velocity: about 20 cm/hour), to collect an IgG-containing eluate. The absorbance of the collected IgG-containing eluate for 280 nm was measured with an absorptiometer, and the measured absorbance was converted with the absorption constant to determine the concentration of each antibody.

(Evaluation of Antibody)

The 7938 antibody among the monoclonal antibodies purified by the affinity chromatography described above was evaluated using ALB solutions of different concentrations under the same conditions as those in the inhibition ELISA method in the second-stage selection described above, except for the solid-phase antigen concentration ($1\times10^{-8}$ M) and the antibody concentration ($1\times10^{-10}$ M).

Figure 6:
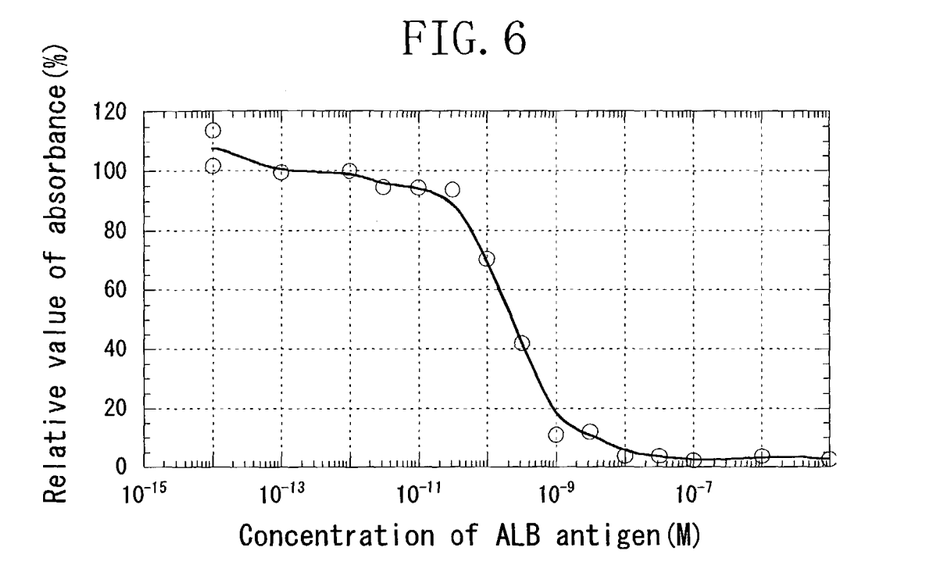
FIG. 6 is a graph showing the results of an inhibition ELISA method using 7938 antibody.

FIG. 6 is a graph showing the results of measurement of the binding ability to ALB of the 7938 antibody. In FIG. 6, the y-axis represents the relative value (%) of the absorbance and the x-axis represents the concentration (mole/L (herein, referred to as M)) of the ALB antigen. The relationship between the concentration of the antigen and the relative value (%) of the absorbance is shown by the solid line.

As shown in FIG. 6, as for the 7938 antibody, the half value of inhibition is about $1\times10^{-9.8}$ M, and it is indicated that ALB can be detected in the range of concentration of about $1\times10^{-9}$ M to about $1\times10^{-11}$ M.

The 7937 antibody among the monoclonal antibodies purified by the affinity chromatography described above was evaluated using ALB diluted series under the same conditions as those in the inhibition ELISA method in the second-stage selection described above, except for the solid-phase antigen concentration ($1\times10^{-7}$ M) and the antibody concentration ($1\times10^{-7}$ M).

Figure 7:
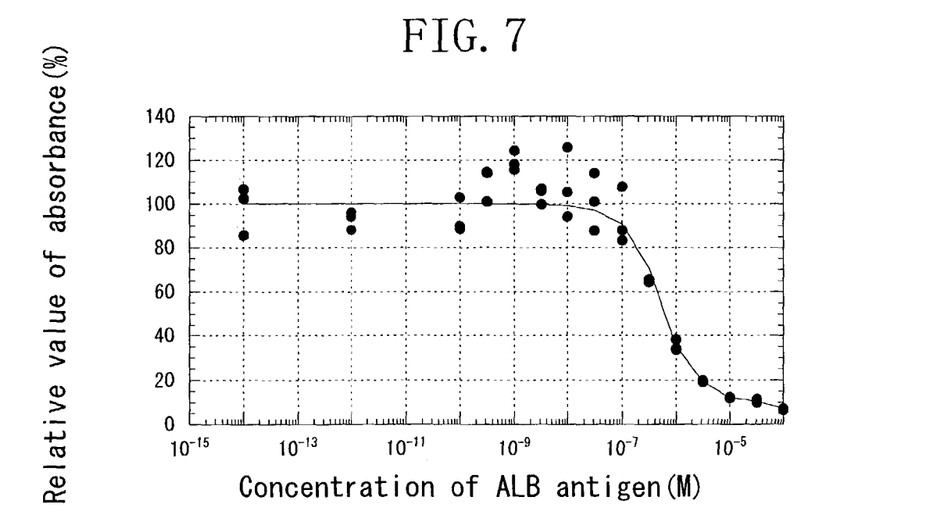
FIG. 7 is a graph showing the results of the inhibition ELISA method using 7937 antibody.

FIG. 7 is a graph showing the results of measurement of the binding ability to ALB of the 7937 antibody. In FIG. 7, the y-axis represents the relative value (%) of the absorbance and the x-axis represents the concentration (M) of the ALB antigen. The relationship between the concentration of the antigen and the relative value (%) of the absorbance is shown by the solid line.

As shown in FIG. 7, as for the 7937 antibody, the half value of inhibition is about $1\times10^{-6.3}$ M, and it is indicated that ALB can be detected in the range of concentration of about $1\times10^{-7}$ M (6.6 mg/L) to about $1\times10^{-5}$ M (660 mg/L).

The 8307 antibody among the monoclonal antibodies purified by the affinity chromatography described above was evaluated using ALB diluted series under the same conditions as those in the inhibition ELISA method in the second-stage selection described above, except for the solid-phase antigen concentration ($1\times10^{-7}$ M) and the antibody concentration ($1\times10^{-7}$ M).

Figure 8:
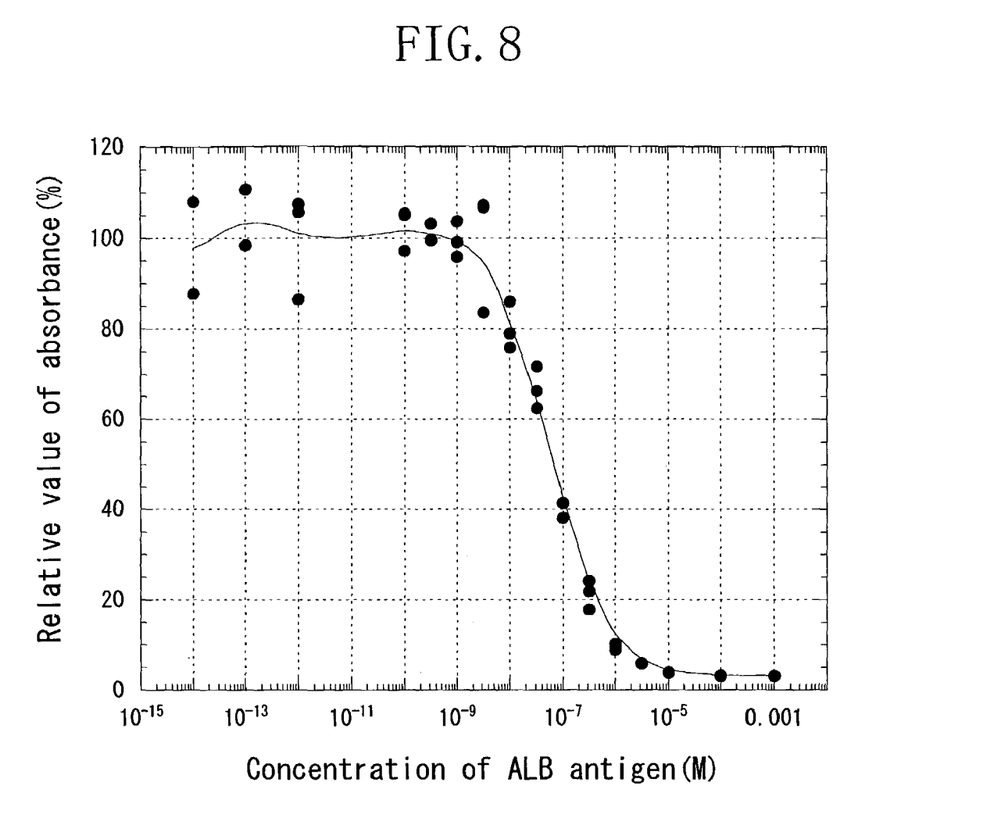
FIG. 8 is a graph showing the results of the inhibition ELISA method using 8307 antibody.

FIG. 8 is a graph showing the results of measurement of the binding ability to ALB of the 8307 antibody. In FIG. 8, the y-axis represents the relative value (%) of the absorbance and the x-axis represents the concentration (M) of the ALB antigen. The relationship between the concentration of the antigen and the relative value (%) of the absorbance is shown by the solid line.

The 8308 antibody among the monoclonal antibodies purified by the affinity chromatography described above was evaluated using ALB diluted series under the same conditions as those in the inhibition ELISA method in the second-stage selection described above, except for the solid-phase antigen concentration ($1\times10^{-7}$ M) and the antibody concentration ($1\times10^{-7}$ M).

Figure 9:
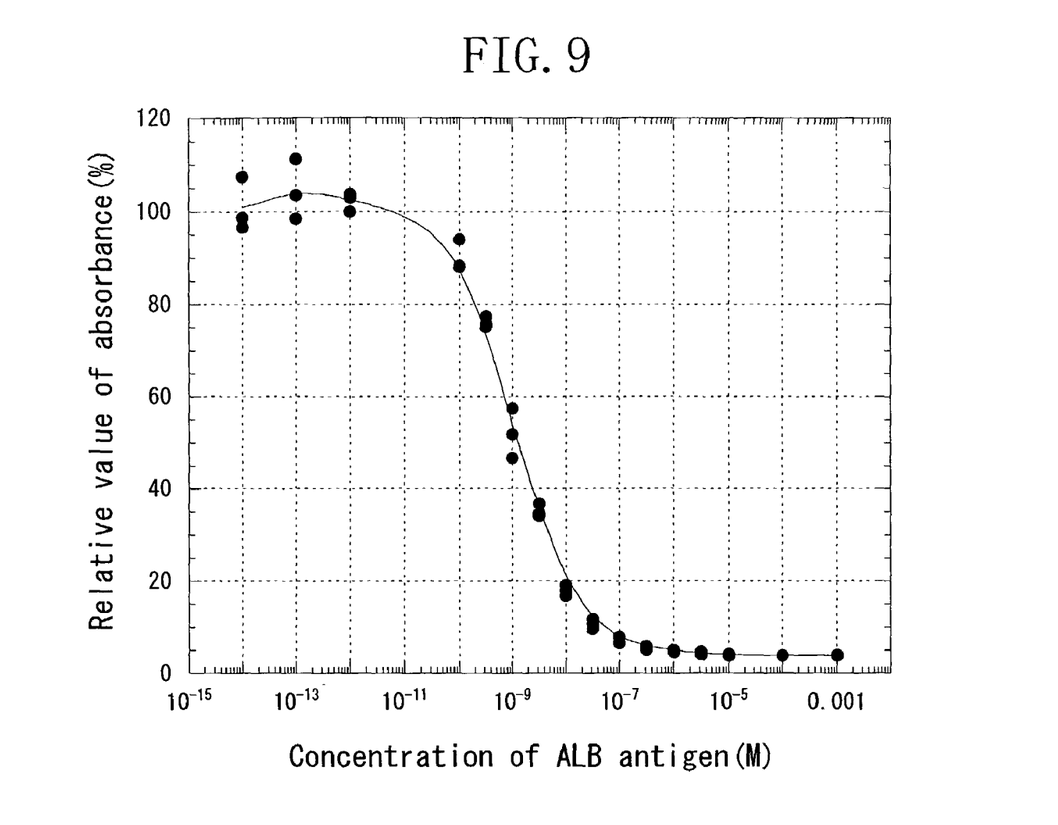
FIG. 9 is a graph showing the results of the inhibition ELISA method using 8308 antibody.

FIG. 9 is a graph showing the results of measurement of the binding ability to ALB of the 8308 antibody. In FIG. 9, the y-axis represents the relative value (%) of the absorbance and the x-axis represents the concentration (M) of the ALB antigen. The relationship between the concentration of the antigen and the relative value (%) of the absorbance is shown by the solid line.

The 8309 antibody among the monoclonal antibodies purified by the affinity chromatography described above was evaluated using ALB diluted series under the same conditions as those in the inhibition ELISA method in the second-stage selection described above, except for the solid-phase antigen concentration ($1\times10^{-7}$ M) and the antibody concentration ($1\times10^{-7}$ M).

Figure 10:
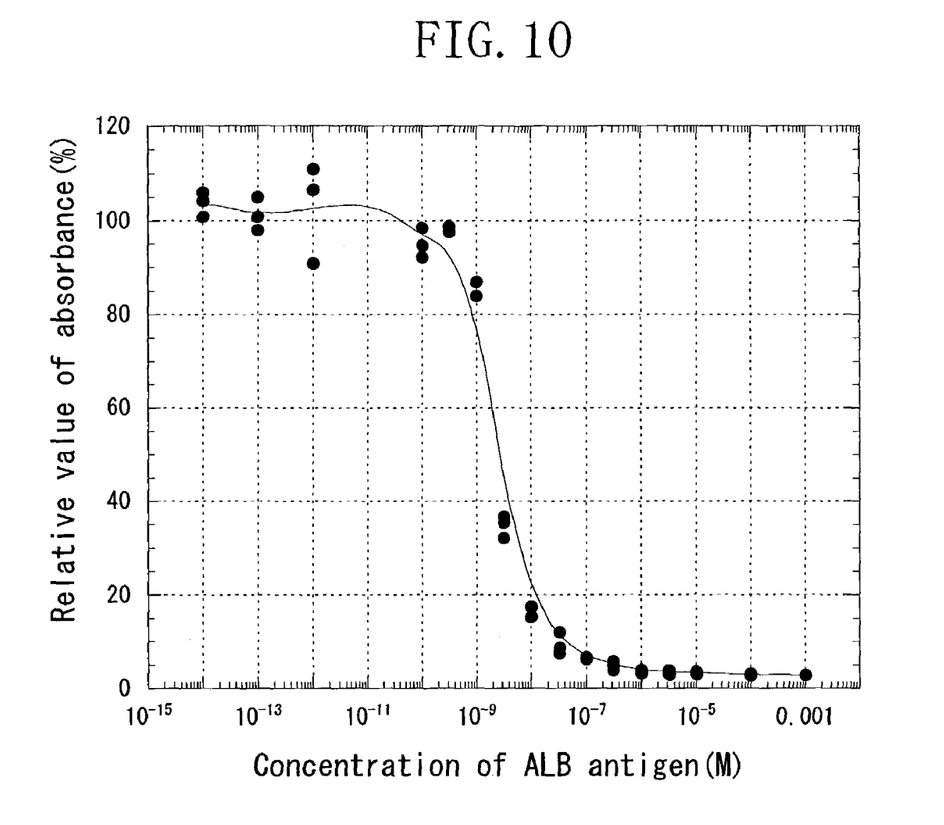
FIG. 10 is a graph showing the results of the inhibition ELISA method using 8309 antibody.

FIG. 10 is a graph showing the results of measurement of the binding ability to ALB of the 8309 antibody. In FIG. 10, the y-axis represents the relative value (%) of the absorbance and the x-axis represents the concentration (M) of the ALB antigen. The relationship between the concentration of the antigen and the relative value (%) of the absorbance is shown by the solid line.

In the examples described above, human albumin was used as the subject substance. Alternatively, albumin of mammals other than the human, human luteinizing hormone (hLH) and human chorionic gonadotropin (hCG) that are urinary hormones serving as an indicator for women's healthcare, and the like may be measured as the subject substance. In measurement of hLH and hCG, a succinic acid buffer may be added to the sample to attain high turbidity. By this addition, the prozone phenomenon can be suppressed during the measurement of hLH and hCG. In particular, the highest turbidity can be obtained if the sample is prepared to have pH 5.0 by adding the succinic acid buffer to the sample. A MOPS buffer may also be used depending on the type of the monoclonal antibody used. If a MOPS buffer is used, it is particularly preferred to prepare the sample to have pH 7.4.

While the present invention has been described in preferred embodiments, it will be apparent to those skilled in the art that the disclosed invention may be modified in numerous ways and may assume many embodiments other than that specifically set out and described above. Accordingly, it is intended by the appended claims to cover all modifications of the invention which fall within the true spirit and scope of the invention.

The hybridomas disclosed herein were deposited in compliance with the Budapest Treaty at the International Patent Organism Depositary, National Institute of Advanced Industrial Science and Technology, AIST Tsukuba Central 6, 1-1, Higashi 1-Chome Tsukuba-shi, Ibaraki-ken 305-8566 Japan. The deposits were made on the following dates: ERM BP-7938: Mar. 7, 2002, FERM BP-7937: Mar. 7, 2002, FERM BP-8307: Feb. 27, 2003, FERM BP-8308: Feb. 27, 2003, FERM BP-8309: Feb. 27, 2003.

What is claimed is:

1. An anti-albumin monoclonal antibody produced from a cell strain deposited as Accession Number FERM BP-7938.

2. An anti-albumin monoclonal antibody produced from a cell strain deposited as Accession Number FERM BP-7937.

3. An anti-albumin monoclonal antibody produced from a cell strain deposited as Accession Number FERM BP-8307.

4. An anti-albumin monoclonal antibody produced from a cell strain deposited as Accession Number FERM BP-8308.

5. An anti-albumin monoclonal antibody produced from a cell strain deposited as Accession Number FERM BP-8309.

6. A cell strain deposited as Accession Number FERM BP-7938.

7. A cell strain deposited as Accession Number FERM BP-7937.

8. A cell strain deposited as Accession Number FERM BP-8307.

9. A cell strain deposited as Accession Number FERM BP-8308.

10. A cell strain deposited as Accession Number FERM BP-8309.

11. An immunoassay method for measuring a content of human albumin in a sample, comprising the steps of:
   (a) providing an antibody solution including a first monoclonal anti-albumin antibody, a second monoclonal anti-albumin antibody and a third monoclonal anti-albumin antibody all capable of specifically binding to different epitopes of human albumin, wherein each of the epitopes bound by the first and the second monoclonal antibodies exists singly in albumin, and wherein the first monoclonal antibody is a monoclonal antibody produced from a cell strain deposited as Accession Number FERM BP-7937;

the second monoclonal antibody is a monoclonal antibody produced from a cell strain deposited as Accession Number FERM BP-7938; and the third monoclonal antibody is a monoclonal antibody produced from a cell strain deposited as Accession Number FERM BP-8307;

(b) preparing a mixed solution by mixing the sample and the antibody solution under conditions sufficient for the monoclonal antibodies to specifically bind to albumin in the sample; and (c) measuring an optical property of the mixed solution, wherein the measured optical property is proportional to the content of human albumin in the sample.

12. An immunoassay method for measuring a content of human albumin in a sample, comprising the steps of:

(a) providing an antibody solution including a first monoclonal anti-albumin antibody, a second monoclonal anti-albumin antibody and a third monoclonal anti-albumin antibody all capable of specifically binding to different epitopes of human albumin, wherein each of the epitopes bound by the first and the second monoclonal antibodies exists singly in albumin, and wherein the first monoclonal antibody is a monoclonal antibody produced from a cell strain deposited as Accession Number FERM BP-7938;

the second monoclonal antibody is a monoclonal antibody produced from a cell strain deposited as Accession Number FERM BP-8308; and the third monoclonal antibody is a monoclonal antibody produced from a cell strain deposited as Accession Number FERM BP-8309;

(b) preparing a mixed solution by mixing the sample and the antibody solution under conditions sufficient for the monoclonal antibodies to specifically bind to albumin in the sample; and (c) measuring an optical property of the mixed solution, wherein the measured optical property is proportional to the content of human albumin in the sample.

13. The immunoassay method claim 11 or 12 wherein the measured optical property is intensity of scattered light or amount of transmitted light.

* * * * *